United States Patent
Popa et al.

(10) Patent No.: US 12,190,857 B2
(45) Date of Patent: Jan. 7, 2025

(54) METAMATERIAL-BASED ACOUSTIC SENSOR BEAMFORMING

(71) Applicant: The Regents of the University of Michigan, Ann Arbor, MI (US)

(72) Inventors: Bogdan Ioan Popa, Ann Arbor, MI (US); Bogdan Epureanu, Ann Arbor, MI (US); Hyung-Suk Kwon, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 303 days.

(21) Appl. No.: 17/743,878

(22) Filed: May 13, 2022

(65) Prior Publication Data
US 2023/0056534 A1 Feb. 23, 2023

Related U.S. Application Data

(60) Provisional application No. 63/188,079, filed on May 13, 2021.

(51) Int. Cl.
*G10K 11/30* (2006.01)
*A61B 8/00* (2006.01)
(Continued)

(52) U.S. Cl.
CPC .............. *G10K 11/30* (2013.01); *A61B 8/00* (2013.01); *B06B 1/067* (2013.01); *G01N 29/221* (2013.01); *H01Q 15/0086* (2013.01)

(58) Field of Classification Search
CPC .. G10K 11/00; G10K 11/18–25; G10K 11/30; H01Q 3/00–20; H01Q 15/00–04;
(Continued)

(56) References Cited

U.S. PATENT DOCUMENTS 11,574,619 B2 * 2/2023 Su .................... G10K 11/32
2012/0328240 A1 12/2012 Ma
(Continued)

OTHER PUBLICATIONS

Allevato G. et al.; Real-time 3D imaging using an air-coupled ultrasonic phased-array; IEEE Transactions on Ultrasonics, Ferroelectrics, and Frequency Control; vol. 68; 2021; pp. 796-806.
(Continued)

*Primary Examiner* — Nguyen Q. Ha
(74) *Attorney, Agent, or Firm* — Lempia Summerfield Katz LLC

(57) ABSTRACT

An acoustic lens to steer an acoustic beam includes a first structure, a second structure spaced from the first structure, an array of projections disposed between the first and second structures, each projection of the array of projections extending from the first structure toward the second structure to define a respective gap between the projection and the second structure, and an actuator configured to move the first structure, the second structure, or the array of projections for collective adjustment of the respective gaps of the array of projections. Each projection is configured to define one or more respective unit cells, each unit cell having a subwavelength size relative to the acoustic beam to establish an effective refractive index profile for the acoustic beam between the first and second structures. The actuator is configured such that the collective adjustment of the respective gaps varies across the array of projections to spatially modify the effective refractive index profile to steer the acoustic beam.

23 Claims, 7 Drawing Sheets

(51) Int. Cl.
  *B06B 1/06* (2006.01)
  *G01N 29/22* (2006.01)
  *H01Q 3/00* (2006.01)
  *H01Q 15/00* (2006.01)

(58) Field of Classification Search
  CPC ........ H01Q 15/0086; A61B 8/00; B06B 1/06; B06B 1/067; G01N 29/22; G01N 29/221
  See application file for complete search history.

(56) References Cited

U.S. PATENT DOCUMENTS

| | | | |
|---|---|---|---|
| 2015/0228269 A1 | 8/2015 | Semperlotti | |
| 2015/0301428 A1 | 10/2015 | Arnold | |
| 2018/0286379 A1* | 10/2018 | Norris | G10K 11/30 |
| 2022/0180853 A1* | 6/2022 | Memoli | G10K 11/30 |

OTHER PUBLICATIONS

B.-I. Popa et al.; Active acoustic metamaterials reconfigurable in real time; Phys. Rev. B, vol. 91; 2015; pp. 220303R.

B.-I. Popa et al.; ARC Project No. 3.A61; Sonar-Based Sensors for Autonomous Vehicles Using Passive and Active Metamaterials; 2019-2020; pp. 1-4.

B.-I. Popa et al.; Broadband sound barriers with bianisotropic metasurfaces; Nature Communications, vol. 9; 2018; pp. 1-7.

Babak S-J et al.; Control of autonomous ground vehicles: a brief technical review; 4th International Conference on Mechanics and Mechatronics Research (ICMMR 2017); IOP Conference Series: Materials Science and Engineering vol. 224; 2017; 012029; pp. 1-7.

C. Jung et al.; Nonlinear Amplitude Approximation for Bilinear Systems, Journal of Sound and Vibration; vol. 333; 2014; pp. 2909-2919.

Caspers P. et al.; A design for a dynamic biomimetic sonarhead inspired by horseshoe bats; Bioinspiration & biomimetics vol. 13; 2018; 046011; pp. 1-11.

Chen Z. et al.; Tunable metasurface for acoustic wave redirection, focusing and source illusion; Journal of Physics D: Applied Physics vol. 52; 2019; 395503; pp. 1-9.

Climente A. et al.; Sound focusing by gradient index sonic lenses; Applied Physics Letters vol. 97; 2010; 104103; pp. 1-3.

D. Li et al.; Design of an acoustic metamaterial lens using genetic algorithms; J. Acoust. Soc. Am., vol. 132; 2012; pp. 2823-2833.

Fokin V. et al.; Method for retrieving effective properties of locally resonant acoustic metamaterials; Physical review B vol. 76; 2007; 144302; pp. 1-5.

Gerard N J et al.; Fabrication and experimental demonstration of a hybrid resonant acoustic gradient index metasurface at 40 kHz; Applied Physics Letters vol. 114; 2019; 231902; pp. 1-6.

H.-S. Kwon et al.; Design and experimental demonstration of broadband acoustic pressure enhancing passive metafluids, Journal of the Acoustical Society of America, vol. 145; 2019; pp. 3633-3639.

International Preliminary Report on Patentability of the International Bureau cited in corresponding international patent application No. PCT/US2022/029173; Nov. 14, 2023; 5 pp.

International Search Report and Written Opinion of the International Searching Authority cited in corresponding international patent application No. PCT/US2022/029173; Sep. 8, 2022; 6 pp.

J. Durnin et al.; Diffraction-free beams, Physical Review Letters, vol. 58; 1987; pp. 1499-1501.

Jiménez F. et al.; Vehicle tracking for an evasive manoeuvres assistant using low-cost ultrasonic sensors; Sensors vol. 14; 2014; pp. 22689-22705.

K. Nakajima et al.; 3D environment mapping and self-position estimation by a small flying robot mounted with a movable ultrasonic range sensor; J. Electrical Systems and Information Technology, vol. 4; 2017; pp. 289-298.

K. Wang et al.; Vibration-Based Identification of Interphase Properties in Long Fiber-Reinforced Composites; Composite Structures vol. 174; 2017; pp. 244-251.

L. Alonso et al.; Ultrasonic sensors in urban traffic driving-aid systems, Sensors, vol. 11; 2011; pp. 661-673.

L. Zigoneanu et al.; Design and measurements of a broadband two-dimensional acoustic lens; Phys. Rev. B, vol. 84; 2011; pp. 024305.

Lan J. et al.; Manipulation of acoustic wavefront by gradient metasurface based on Helmholtz Resonators; Scientific reports vol. 7, 2017; pp. 1-9.

Li Y. et al.; Tunable asymmetric transmission via lossy acoustic metasurfaces; Physical review letters vol. 119; 2017; 035501; pp. 1-5.

Lin S C S et al.; Gradient-index phononic crystals; Physical Review B vol. 79; 2009; 094302; pp. 1-6.

Liu C. et al.; Wide-angle broadband nonreflecting acoustic metamaterial fence; Physical Review Applied vol. 13; 2020; 054012; pp. 1-7.

M. Haberman et al.; Acoustic Metamaterials; Physics Today, vol. 69; 2016; pp. 42-48.

Martin T P et al.; Sonic gradient index lens for aqueous applications; Applied Physics Letters vol. 97; 2010; 113503; pp. 1-3.

Marzo A. et al.; Ultraino: An open phased-array system for narrowband airborne ultrasound transmission; IEEE transactions on ultrasonics, ferroelectrics, and frequency control; vol. 65; 2018; pp. 102-111.

Memoli G. et al.; Metamaterial bricks and quantization of metasurfaces; Nature communications vol. 8; 2017; 14608; pp. 1-8.

Müller R. et al.; Dictionary-Based Learning for 3D-Imaging with Air-Coupled Ultrasonic Phased Arrays; 2020 IEEE International Ultrasonics Symposium (IUS); 2020; pp. 1-4.

Pendry J B et al.; An acoustic metafluid: realizing a broadband acoustic cloak; New Journal of Physics vol. 10; 2008; 115032; pp. 1-9.

Popa B-I et al.; Design and characterization of broadband acoustic composite metamaterials; Physical review B vol. 80; 2009; 174303; pp. 1-6.

Popa B-I et al.; Non-reciprocal and highly nonlinear active acoustic metamaterials; Nature communications vol. 5; 2014; pp. 1-5.

Popa B-I; Broadband sound pressure enhancement in passive metafluids; Physical Review B vol. 96; 2017; 094305; pp. 1-5.

S. A. Cummer et al.; Controlling sound with acoustic metamaterials; Nature Reviews Materials, vol. 1; article No. 16001, 2016; pp. 1-13.

S. Zucca and B. I. Epureanu, Bilinear Reduced-Order Models of Structures with Friction Intermittent Contacts, Nonlinear Dynamics; vol. 77, 2014; pp. 1055-1067.

S. Zucca et al.; Reduced Order Models for Nonlinear Dynamic Analysis of Structures with Intermittent Contacts; Journal of Vibration and Control, vol. 24; 2017; pp. 1-14.

Tian Z et al.; Programmable acoustic metasurfaces; Advanced functional materials vol. 29; 2019; 1808489; pp. 1-8.

Xie Y. et al.; Wavefront modulation and subwavelength diffractive acoustics with an acoustic metasurface; Nature communications vol. 5; 2014; pp. 1-5.

Xu, J. et al.; Acoustic prism for continuous beam steering based on piezoelectric metamaterial; Proceedings SPIE vol. 9799, Active and Passive Smart Structures and Integrated Systems; 2016; pp. 1-10.

Y. Xie et al.; Single-sensor multispeaker listening with acoustic metamaterials, Proceedings of the National Academy of Sciences, vol. 112; 2015; pp. 10595-10598.

Y. Yovel et al.; Optimal localization by pointing off axis, Science, vol. 327; 2010; pp. 701-704.

Yang L. et al.; Design of a dynamic sonar emitter inspired by hipposiderid bats; Bioinspiration & biomimetics vol. 13; 2018; 056003; pp. 1-11.

Zhai Y. et al.; Active Willis metamaterials for ultracompact nonreciprocal linear acoustic devices; Physical Review B vol. 99; 2019; 220301; pp. 1-6.

Zhang L. et al.; Acoustic radiation force expressed using complex phase shifts and momentum-transfer cross sections; The Journal of the Acoustical Society of America vol. 140; 2016; pp. EL178-EL183.

(56) References Cited

OTHER PUBLICATIONS

Zhao L. et al.; Ultrasound beam steering with flattened acoustic metamaterial Luneburg lens; Applied Physics Letters vol. 116 ; 2020; 071902; pp. 1-6.

* cited by examiner

METAMATERIAL-BASED ACOUSTIC SENSOR BEAMFORMING

CROSS-REFERENCE TO RELATED APPLICATION

This application claims the benefit of U.S. provisional application entitled "Metamaterial-Based Acoustic Sensor Beamforming," filed May 13, 2021, and assigned Ser. No. 63/188,079, the entire disclosure of which is hereby expressly incorporated by reference.

STATEMENT REGARDING FEDERALLY SPONSORED RESEARCH OR DEVELOPMENT

This invention was made with government support under Contract No. W56HZV-19-2-0001 awarded by the United States Army. The government has certain rights in the invention.

BACKGROUND OF THE DISCLOSURE

Field of the Disclosure

The disclosure relates generally to abnormality detection in acoustic imaging sensors.

Brief Description of Related Technology

Ultrasound has been used by animals to navigate through environments where optical sensing is not feasible. For instance, bats use ultrasound beams in an energy efficient manner to hunt millimeter size insects in complete darkness. Bats do so by constantly changing the direction of the ultrasound beam many times per second to ensonify the target with the beam's left and then right sides to properly identify the target and keep track of its often hieratic movement.

Inspired by the performance of bat biosonar, researchers have tried to design ultrasonic sensors that replicate the ability of certain animals to project narrow ultrasound beams in desired directions, but the proposed devices have significant limitations. For example, the sensors used in advanced driver assisted systems lack directivity and thus have very limited ranges. Designs that replicate the bat's nose and ear morphology employed pneumatic actuation, but could ensonify only a very limited set of discrete directions, as opposed to continuously scanning the surroundings. Multiple ultrasonic transducers arranged in phased arrays have been shown to be better at mimicking the directivity of a biosonar beam, but such transducers are bulky, expensive and power inefficient.

Metamaterial research has approached the dynamical beam forming and steering challenge from a different perspective. Metamaterials have acoustic properties that can be dynamically modified as desired. However, for most applications of interest, large samples of metamaterials are unfortunately needed.

Past research on reconfigurable media has produced either static structures with fixed acoustic properties, or created methods to change the material parameters over limited spatial scales without the possibility to scale these approaches to larger structures. For example, recent studies on acoustic gradient index (GRIN) lens lenses developed reconfigurable metamaterials that showed a way to tune the lens behavior by adding an actuator to each unit cell or group of cells. Each actuator is then controlled independently. In such cases, small metasurfaces with at most a few dozen unit cells were tuned. Unfortunately, scaling such methods to control larger structures is not feasible due to the large numbers of actuators.

SUMMARY OF THE DISCLOSURE

In accordance with one aspect of the disclosure, an acoustic lens to steer an acoustic beam includes a first structure, a second structure spaced from the first structure, an array of projections disposed between the first and second structures, each projection of the array of projections extending from the first structure toward the second structure to define a respective gap between the projection and the second structure, and an actuator configured to move the first structure, the second structure, or the array of projections for collective adjustment of the respective gaps of the array of projections. Each projection is configured to define one or more respective unit cells, each unit cell having a sub-wavelength size relative to the acoustic beam to establish an effective refractive index profile for the acoustic beam between the first and second structures. The actuator is configured such that the collective adjustment of the respective gaps varies across the array of projections to spatially modify the effective refractive index profile to steer the acoustic beam.

In accordance with another aspect of the disclosure, an acoustic device includes a transducer configured to generate an input sound wave, a waveguide coupled to the transducer to receive the input sound wave, a beam former including an input aperture coupled to the waveguide, an output aperture, and a gradient index lens disposed between the input and output apertures, the gradient index lens having a continuous refractive index profile. The gradient index lens includes a first structure, a second structure spaced from the first structure, an array of projections disposed between the first and second structures, each projection of the array of projections extending from the first structure toward the second structure to define a respective gap between the projection and the second structure, and an actuator configured to move the first structure, the second structure, or the array of projections for collective adjustment of the respective gaps of the array of projections. The actuator is configured such that the collective adjustment of the respective gaps varies across the array of projections to spatially modify an effective refractive index of the gradient index lens.

In connection with any one of the aforementioned aspects, the devices and/or methods described herein may alternatively or additionally include or involve any combination of one or more of the following aspects or features. The actuator is configured to move the second structure. One of the first and second structures is flexible. The actuator is configured to rotate one of the first and second structures about an axis parallel to a propagation direction of the acoustic beam prior to steering. One of the first and second structures includes an array of piezoelectric patches. The actuator includes a plurality of voltage sources configured to apply a position-dependent voltage to the array of piezoelectric patches. The actuator includes a plate that acts on one of the first and second structures. The collective adjustment of the respective gaps varies in a direction transverse to a propagation direction of the acoustic beam prior to steering. Each projection of the array of projections has a respective length. The respective length of the projections varies along a propagation direction of the acoustic beam to provide impedance matching. The first and second structures define input and output apertures through which the acoustic beam enters and exits the slot, respectively. The array of projections includes input and output impedance matching sections at the input and output apertures, respectively. The projections have respective heights in the input and output impedance matching sections that progressively range up to, and down from, a primary height of the projections, respectively. The first and second structures include first and second plates, respectively. The array of projections are disposed in a periodic arrangement. The transducer is a point source such that the input sound wave is cylindrical. The waveguide includes a parallel plate waveguide configured to direct the input sound wave to the input aperture of the acoustic lens. The actuator is configured to rotate one of the first and second structures about an axis parallel to a propagation direction of the acoustic beam prior to steering. The collective adjustment of the respective gaps varies in a direction transverse to a direction of propagation through the input aperture. Each projection of the array of projections has a respective length. The respective length of the projections varies along a propagation direction of the acoustic beam to provide impedance matching. The array of projections includes input and output impedance matching sections at the input and output apertures, respectively. The projections have respective heights in the input and output impedance matching sections that progressively range up to, and down from, a primary height of the projections, respectively. The first and second structures include first and second plates, respectively. The array of projections are disposed in a periodic arrangement.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 1:
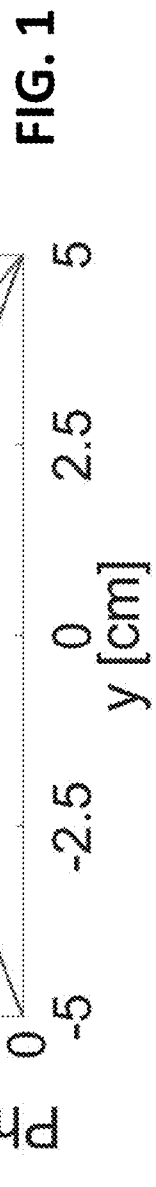
FIG. 1 depicts a schematic view of an acoustic device having a metamaterial acoustic lens with a gradient index (GRIN) profile for beam steering in accordance with one example, along with a schematic representation of phase advances of an acoustic ray propagating through the acoustic GRIN lens and a plot of phase profiles of the GRIN lens for beam forming and steering.

The embodiments of the disclosed devices may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Acoustic devices having an acoustic lens with a gradient index profile for steering of an acoustic beam are described. The acoustic lens includes an assembly of structures that includes an array of projections, with each projection defining one or more unit cells, each unit cell having a sub-wavelength size relative to the acoustic beam. The sub-wavelength size establishes an effective refractive index profile (e.g., of a metamaterial of the acoustic lens) for the acoustic beam. Collective adjustment of respective gaps of the array of projections (as opposed to individual or independent adjustment) is used to spatially modify the effective refractive index profile to steer the acoustic beam.

The disclosed devices may be configured as a biosonar-like device that takes a diverging acoustic wave, e.g., produced by a ultrasound transducer, and passes the wave through a tunable acoustic gradient index (GRIN) lens to form collimated, directive beams that may then be steered in prescribed directions. The lenses of the disclosed devices have a sufficiently large aperture to form a highly directive beam. The lenses also impose a prescribed inhomogeneous phase advance throughout the lens. Furthermore, the sound phase advance through the lens varies drastically from one part of the device to the next. The disclosed devices also provide a sufficiently high phase advance gradient to allow for a thin lens. The disclosed devices also address another challenge presented by large phase gradients—i.e., resonances that impose narrow band operation. But narrow band operation is undesirable in acoustics because most applications (e.g., sonar—including biosonar, medical imaging, etc.) rely on the manipulation and processing of short pulses and thus involve broadband operation. In contrast, the scalability of the acoustic lens of the disclosed devices allows the disclosed devices to be capable of supporting broadband operation, as described herein.

The disclosed acoustic devices may be useful as ultrasound or other acoustic sensors for various applications, including, for instance, those involving scanning and imaging of the surrounding environment, such as sensors for autonomous or semi-autonomous vehicles, ultrasound medical imaging, and sonar. The disclosed acoustic sensors are useful in such applications because sound is far reaching in various types of media, such as air and water. Moreover, when operated in air, the disclosed acoustic sensors maintain efficiency in adverse weather unlike cameras, LIDAR, and radar.

The disclosed acoustic devices differ from past acoustic sensors, which have either very low ranges (e.g., past ultrasound sensors for autonomous vehicles), or involve arrays of speakers and are thus expensive, power hungry, and low-resolution (e.g. sonar, ultrasound imaging). Instead, the disclosed acoustic devices may provide sensors in which sound produced by a single acoustic source (e.g., a speaker or piezoelectric transducer) is focused into a beam by a reconfigurable acoustic lens. Adjustment of the geometry of the acoustic lens (e.g., sub-millimeter dynamical deformations of the lens geometry) direct the beam in desired directions without rotating the entire device, which leads to significant power reduction and increased sensor reliability. The sound scattered by the environment may be captured by the acoustic lens and formed into an image. Non-linear effects in the lens structure may also be used to improve sensor resolution, as described herein.

The metamaterial of the disclosed acoustic devices has scalable properties that are dynamically reconfigurable on-demand and in real time. Past metamaterials have unfortunately been limited to tuning very small samples composed of at most few dozen unit cells. Past approaches have thus not been scalable to larger structures. In contrast, the disclosed acoustic devices may include a mechanism that involves only a single controller to change the acoustic properties of a large-scale, or bulk metamaterial assembly. The mechanism relies on an array of unit cells. A large collection of the unit cells may have acoustic properties collectively set through adjustments (e.g., submillimeter deformations) of a structure of the assembly, such as a flexible plate or other component. Examples of the acoustic devices are described below that demonstrate a reconfigurable metamaterial-based device for highly directive ultrasonic beam forming and steering at 40 kHz.

In some cases, the disclosed acoustic devices include a large amount (e.g., about ten thousand) unit cells reconfigured simultaneously, or collectively, to implement desired, inhomogeneous gradients (as opposed to discrete changes) of the refractive index. As a result, large scale, bulk structures may be provided with a much smaller per cell acoustic response than thin structures (e.g., metasurfaces), and thus do not rely on narrowband resonances and are consequently broadband. The disclosed examples exhibit a bandwidth at least an order of magnitude larger than past metamaterials, including metasurfaces. The reconfigurability of the bulk metamaterials of the disclosed acoustic devices supports wave control over large scales and broadband operation.

Although described in connection with ultrasound sensors and imaging, the disclosed acoustic devices may be used in connection with a wide variety of frequency ranges, media, and use contexts. The disclosed acoustic devices are also not limited to parallel plate structures or assemblies. The disclosed devices may use a wide variety of structures to support and otherwise form a metamaterial-based acoustic lens. The nature of the configurability may also vary considerably. For instance, the geometry of the lens may be adjusted via tilting, deformation, vibration, and/or other movement. The adjustments may be driven by a wide variety of actuators, including, for instance, various electric motor- or electromagnet-based actuators. The shape, construction, and other characteristics of the projections may also vary from the examples shown. For instance, a wide variety of fins, teeth, or pillars may be used. The composition of the projections may also be used to support the configurability. For instance, the projections may be composed of, or otherwise include, a piezoelectric material such that the length (or height) of the projections varies. In such cases, the actuator of acoustic lens may include one or more voltage sources to drive the piezoelectric material.

Although described in connection with examples having a single actuator, the disclosed devices may include multiple actuators. For instance, the devices may include two or more actuators directed to moving respective portions of the structures, e.g., in opposite directions. For example, two or more pin- or probe-shaped actuators may push a sheet- or plate-shaped structure, such as an elastic sheet, to a varying extent. The pin-shaped actuators may be elongated or otherwise extend along the propagation direction. In other cases, the structure may be driven by a pair of actuators may be disposed at either side or end of the structure. Each of the actuators in such cases may nonetheless be considered to collectively adjust the gaps for an array of projections, even though the device may include further projections collectively addressed by another one of the actuators. In such cases, the disclosed devices may thus be considered to include multiple arrays (or sub-arrays) of projections. The projections in each such array (or sub-array) are collectively, rather than individually, actuated and controlled, as described herein.

Described herein are metamaterial-based assemblies that manipulate acoustic properties of large material structures at ultrasonic and other frequencies with a single controlling element. Tuning may be implemented by small (submillimeter) deformations of a single structural element that spans the metamaterial volume. The mechanism was demonstrated experimentally though examples in which an ultrasonic beam steering device operated in a bandwidth of 10% centered at 40 kHz. The example device is 12 wavelengths in width, 6 wavelengths thick, and includes more than 7800 reconfigurable unit cells, which is two orders of magnitude more unit cells than possible with other methods. Moreover, the metamaterial-based assembly is designed to have small insertion loss enabled by the non-resonant nature of the unit cells thereof and by using impedance matching layers or sections. The ultrasound beam formers described herein produce very directive beams that can scan directions spanning 30 degrees. The single transducer approach coupled with the sub-millimeter actuation of one structural element makes the disclosed devices ultra-low power. The reconfigurable aspect of the disclosed devices opens the path to large-scale, smart materials for ultrasonic imaging and other applications.

Part (a) of FIG. 1 depicts a device 100 that provides an example of the reconfiguration of the behavior of bulk metamaterials. In this example, an inhomogeneous refractive index profile is established inside a large metamaterial block or lens 102 of the device 100. In this case, the metamaterial-based device 100 replicates the ability of biosonar-capable animals to raster scan the environment with very directive ultrasound beams. The beam forming and steering is done by the metamaterial lens 102 whose inhomogeneous refractive index profile is dynamically changed. Because the beam width is indirectly proportional to the device aperture, the device 100 may have an aperture of 12 wavelengths (e.g., at the operational frequency of 40 kHz), which is one order of magnitude larger than other static or reconfigurable acoustic lenses. Second, to minimize absorption and increase the bandwidth, the lens 102 includes a metamaterial made of non-resonant unit cells, which have much weaker acoustic responses than the resonant cells used in traditional acoustic lenses. Consequently, the metamaterial may be thick in the propagation direction in order to produce the acoustic phase advance used for beam forming and steering. In this example, the lens is 6 wavelengths in the propagation direction, i.e. one order of magnitude larger than other designs. To increase lensing performance and decrease the amplitude of side lobes, continuous phase advances throughout the lens 102 are provided, as opposed to the step-wise approximations of these profiles implemented by other metamaterials.

Part (a) of FIG. 1 shows the structure of the ultrasound device 100. Cylindrical waves 104 produced by an omnidirectional transducer are guided by a parallel-plate waveguide to an input aperture 106 of the reconfigurable, metamaterial-based GRIN lens 102. In the example of FIG. 1, the reconfigurable metamaterial-based GRIN lens 102 transforms the cylindrical waves 104 from the point source of the transducer into a beam 108 of plane waves and continuously steers the beam 108. The GRIN lens 102 thus forms a collimated beam propagating under an angle with respect to the normal direction x by establishing a refractive index profile inside the lens 102 that varies in the transverse y direction according to the following expression:

$$n(y) = n_0 \text{sech}\left(\frac{\pi y}{2(L_f + L_x)}\right) + \frac{y \sin(\theta_s)}{L_y}$$

where $L_f$ is the focal length of the lens and the distance between the lens input aperture 106 and the transducer, $L_x$ and $L_y$ are the lens dimensions in the x and y directions, and $n_0$ is the refractive index in the middle of the lens 102. The first term of the equation represents the refractive index of a gradient index (GRIN) having a hyperbolic tangent refractive index profile. This profile may be used to reduce lens aberrations and thus improve the quality of the collimated beam produced by the lens. This refractive index component corresponds to a phase advance in the lens for normal incidence of—

$$\phi'(y) = k_{air} L_x n_0 \text{sech}\left(\frac{\pi}{2} \cdot \frac{y}{L_f + L_x}\right)$$

The second term of the equation represents the additional refractive index used to steer the propagating wave. For a sound ray propagating through the GRIN lens 102 to be steered at an angle $\theta_s$ its phase advance ($\phi$) versus the transverse direction y is as follows.

$$\Delta\phi(y) = k_{air} y \sin \theta_s$$

The refractive index for steering is obtained by dividing the phase advance by $k_{air} L_x$, which yields the second term of the equation above.

The maximum index of refraction realizable with non-resonant metamaterial cells is approximately 2, which puts a constraint on the lens dimensions. In one example, $L_x=5$ cm, $L_y=10$ cm, and $L_z=15$ cm, which provides a good tradeoff between the lens size and its performance. Other dimensions may be used.

Because the lens 102 is designed to steer beams in, for instance, a range of +15 degrees to −15 degrees, the plane wave decomposition of the acoustic field through the lens 102 may contain wave vectors with negligible components in they direction. As a result, the phase advance through the lens 102, defined as the phase difference between the input and output apertures normalized to the phase delay in air, may be approximated by $$\theta(y) = k_0 [n(y) - 1] L_x$$

where $k_0$ is the wave number in air, and a phase advance of 0 corresponds to propagation in air.

Part (b) of FIG. 1 shows a number of phase profiles of the metamaterial-based lens 102. Specifically, part (b) depicts a plot of the variation of the phase advance along the direction y for 0 degrees and 15 degrees. The plot shows that high phase advances of almost 1100 degrees are needed through the lens 102. Most past acoustic lenses leverage the periodicity of the phase to implement discontinuous refractive index profiles to impose phase advances in the range 0 to 360 degrees similar to fisheye lenses in optics. This typically means that the lens is divided into sections, and each lens section must be configured independently to obtain dynamic steering. In this case, instead, to configure the lens 102 via a single controller, the lens 102 has a continuous refractive index profile. An unprecedentedly high phase advance may thus be attained by increasing the lens thickness in the propagation direction, e.g., to 6 wavelengths.

The beam forming and steering element is implemented with arrangements of subwavelength (e.g., highly subwavelength) unit cells that form an effective medium with the configurable refractive index profile shown in part (b) of FIG. 1. To satisfy the subwavelength constraint, unit cell dimensions of 0.8 mm by 0.8 mm may be used in one example. In this case, the cell is more than 10 times smaller than the wavelength of 40 kHz sound in air (8.6 mm). The unit cell width of 0.8 mm in a 10 cm by 5 cm metamaterial results in 7,800 unit cells that are configured simultaneously or collectively (as opposed to individually or independently) to implement the inhomogeneous refractive index profiles (e.g., part (b) of FIG. 1). The sheer number of cells to be tuned or adjusted makes previous cell configuration mechanisms that involved controlling each cell or small groups of cells independently unfeasible.

Figure 2:
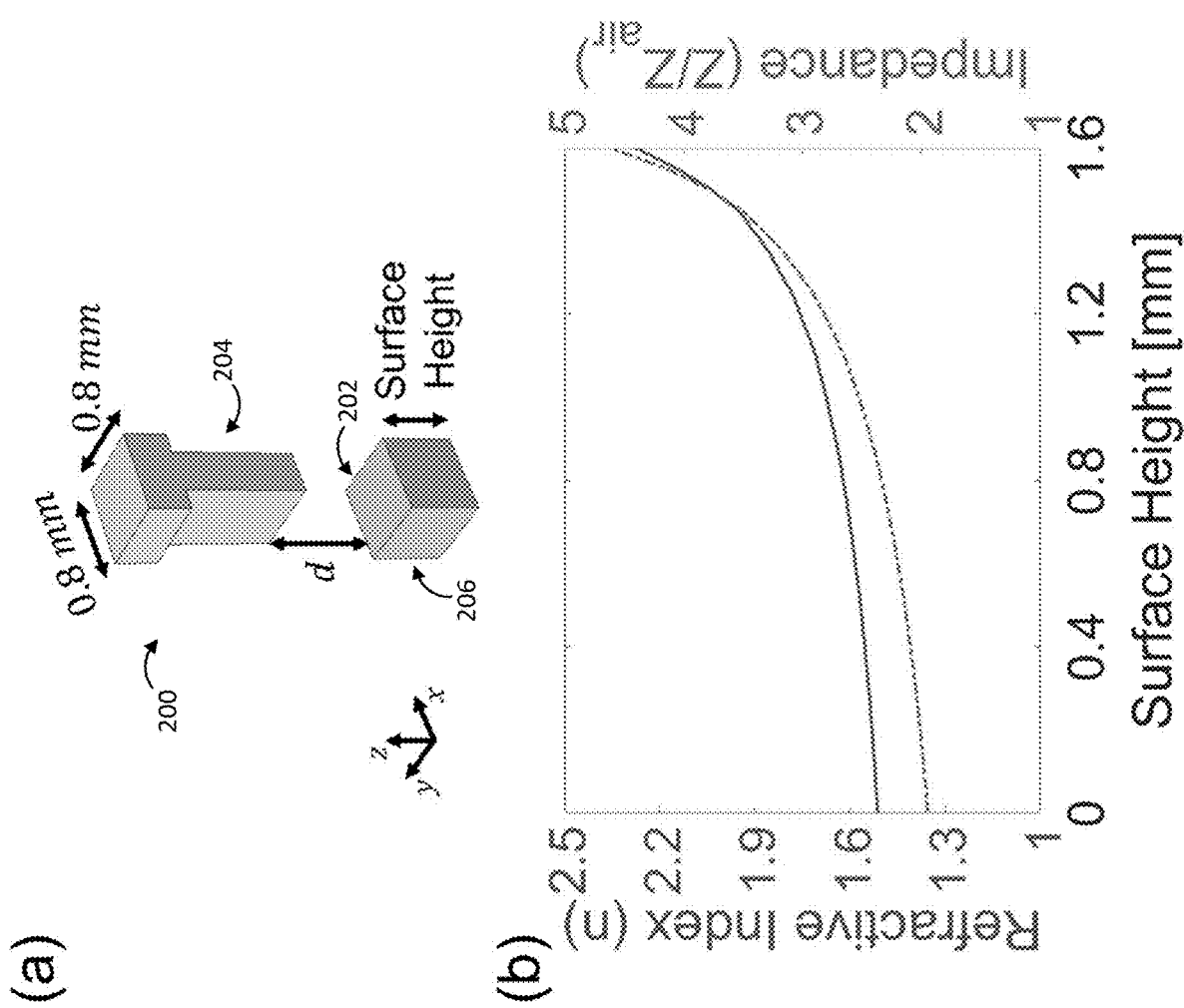
FIG. 2 depicts a schematic, perspective view of a unit cell of a metamaterial acoustic lens having a gap or perforation in accordance with one example, along with a graphical plot of effective refractive index and impedance as a function of gap or perforation size.

Part (a) of FIG. 2 schematically shows a unit cell 200 in accordance with one example. The unit cell 200 may be used in a metamaterial-based lens, such as the lens 102 of FIG. 1. In this example, a bottom surface 202 of the unit cell 200 moves vertically to tune acoustic properties of the unit cell. Part (b) of FIG. 2 shows the effective refractive index and normalized impedance of the unit cell 200 over a range of surface heights.

The cell structure may be configured to facilitate the adjustment of a large number of unit cells. Part (a) of FIG. 2 shows the structure of the unit cell 200. The functionality of the unit cell 200 is based on the observation that sound propagating through perforated solids is delayed by a significant amount and thus perforated solids behave as high refracted index media. The delay increases while the gap or perforation size (indicated with d) decreases. To manipulate large numbers of unit cells with a single controller or actuator, the assembly includes two separate inclusions 204, 206. In some cases, one inclusion is fixed, while the other is mobile. In the example shown, the inclusion 204 (e.g., top inclusion) is fixed and the inclusion 206 (e.g., the bottom surface 202) is mobile. The effective refractive index established by the unit cell 200 is adjusted by moving the lower inclusion 206, or component, relative to the top inclusion 204, or part. This example unit cell assembly strikes a balance between obtaining high phase advances through the cell 200, thereby reducing absorption, and maintaining good manufacturability. In other cases, the roles of the top and bottom inclusions or components 204, 206 may be reversed. In still other cases, both inclusions or components 204, 206 may be mobile, including, for instance, cases in which one of the components is vibrating.

Part (b) of FIG. 2 shows the effective refractive index and insertion loss (due to both absorption and reflection) versus perforation size d for the device 200 shown in part (a) of FIG. 2. These values are calculated from the incident, reflected, and transmitted pressures obtained from simulations using a method widely used for calculating effective acoustic properties of metamaterials.

Acoustic absorption poses a greater challenge at ultrasonic frequencies than at audible frequencies. The reason lies in the high dissipation due to thermoviscous effects occurring in thin layers at the boundary between air and the solids. The thickness of these high loss layers varies weakly with frequency. Simply scaling down the geometry of metamaterials designed to work at few kilohertz (i.e., the vast majority of metamaterials reported so far) to operate at tens of kilohertz means that the smaller spaces through which sound is forced to propagate (such as the gap defined by the parameter d in part (a) of FIG. 2) may become dominated by the high dissipation layers. To keep the absorption small, the minimum gap size d may be 0.4 mm, which ensures a maximum absorption of approximately 0.15 dB/cell. However, this choice limits the refractive index to values under 2, and thus the phase advance defined in the equation above is limited to values below 16 degrees. Consequently, the lens uses more than 60 unit cells in the propagation direction to achieve the desired phase advance of 1100 degrees. This equates to a total expected absorption loss of 8 dB. Remarkably, this is significantly less than is capable of being obtained in a much thinner metasurface that would force sound to propagate through fluid-solid interface layers of high thermoviscous loss.

A second source of insertion loss involves reflections of poorly matched unit cells to the air background. To minimize such reflections, the assembly may include impedance matching sections at the input and output apertures, examples of which are described hereinbelow.

Figure 3:
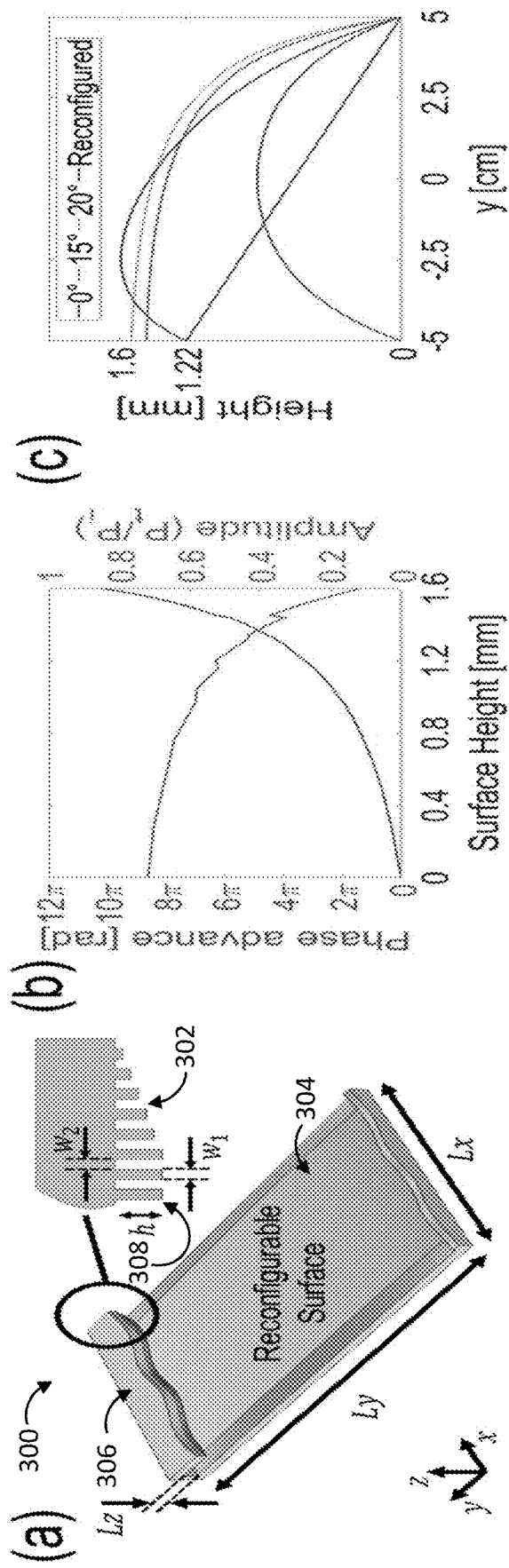
FIG. 3 depicts a partial, schematic, perspective view of an acoustic lens having impedance matching sections in accordance with one example, along with cross-sectional views of acoustic lens with different gap sizes, and graphical plots of the phase advance, amplitude, and geometry profile of the acoustic lens.

Part (a) of FIG. 3 shows the geometry of a reconfigurable metamaterial GRIN lens 300 in accordance with one example. In this example, the lens thickness ($L_x$) and width ($L_y$) are 5 cm and 10 cm respectively. For the height ($L_x$) of the lens, a small height may result in excessive thermal and viscous loss due to narrow path. A height larger than the wavelength may allow multiple modes of sounds to propagate through the lens. Therefore, the lens height may be set to be 3 mm in this example, which is smaller than the wavelength but large enough to keep the losses small. Other heights may be used. Also, the highly subwavelength 0.8 mm by 0.8 mm unit cells are composed of 0.41 mm thick ($w_1$) inclusions with 0.39 mm gaps ($w_2$), but the dimensions may vary. In this case, the 0.41 mm thickness and 0.39 mm gaps are useful because if the gaps are too narrow, then the sounds passing through that region may experience excessive thermal and viscous loss from narrow channel. For the height of the inclusions (h), tall inclusions create large delays from small d but high viscous losses from narrow path. Therefore, the inclusion height may be 1.2 mm in this case to compromise between phase delay range and thermal and viscous losses. Other heights may be used.

Also, as previously mentioned, the lens 300 may include impedance matching sections 302 because the unit cells with high refractive index have much larger impedance than air. This part of the lens 300 is useful because, without impedance matching, only a small portion of incident sound may be transmitted due to excessive insertion loss, making the lens not practical. Therefore, in this example, each impedance matching section 302 includes 4 mm deep or thick matching layers with inclusion height increasing gradually by 0.2 mm. In some cases, a bottom surface 304 of the lens may vary linearly to prevent sudden increase of impedance and thus minimize insertion loss.

As shown by the graphical plot in part (b) of FIG. 3, changing perforation size d changes wave length inside the metamaterial and thus changes phase at the exit. Phase and amplitude of the transmitted acoustic wave for the entire surface height range used in the lens design are presented in part (c) of FIG. 3.

Similar to the unit cell analysis, the cross section confirms that considerable phase change of about 7·π is achievable with about 1.5 mm deflection of the surface. However, due to reflections and thermal losses, the amplitude of transmitted waves is small for gap sizes (d) smaller than about 0.9 mm. The impedance matching sections 302 become less efficient as the gap size decreases because the impedance gap between the plateau region and outside the lens increases. Also, losses from air viscosity and thermal effects are more dominant for narrow channels as well. As a result, in connection with a gap size range of about 0.9 mm to about 1.8 mm where phase change is relatively linear, transmitted pressure is large. For a gap size range of about 0.3 mm to about 0.9 mm, on the other hand, phase change is exponential, and transmitted pressure is small.

Replicating (e.g., periodically replicating) the unit cell shown in FIG. 2 in the x and y directions results in a metamaterial lens whose geometry is shown in part (a) of FIG. 3. In this example, the lens 300 includes a fixed top element 306 containing fins 308 of height h and width $w_1$ spaced a distance $w_2$ apart. Each fin 308 is disposed in a respective row that runs along the direction of the y-axis shown in FIG. 3. Each fin 308 may thus include, and be realized by stacking, multiple unit cells (e.g., 190 cells) in the y-axis direction. The lens 300 provides a steerable angle between −20 degrees and 20 degrees for a steerable range of 40 degrees. In this case, the bottom element 304 is a flexible component whose topology is chosen to realize the desired behavior of the metamaterial. For instance, a configurable beam former may have the desired phase advance shown in part (b) of FIG. 1. The equation above may be used to compute the refractive index versus position inside the lens, and part (b) of FIG. 2 may be used to map the refractive index to the gap size d for each unit cell and thus find the shape of the flexible component throughout the metamaterial. In this example, the refractive index varies in the transverse y direction only. Therefore, the topology of the flexible element 304 varies only in the y direction in this implementation. In other cases, additional variation may be provided.

Part (b) of FIG. 3 shows the ability of the metamaterial to control the phase advance in a range 0 to 1260 degrees. Numerical simulations performed with Comsol Multiphysics that take into account the thermoviscous losses inside the complicated structure show that the transmission coefficient remains above 0.5 across the entire range.

Part (c) of FIG. 3 shows the topology of the flexible component 304 versus y for two steering angles of 0 degrees and 20 degrees. These example topologies exhibit several useful aspects of the small phase advance per unit cell afforded by bulk metamaterials. In this case, the flexible component is smooth, has a small gradient in x and y, and the maximum deformation is below 1.5 mm.

A variety of different actuators or mechanisms may be used to change the shape of the flexible component(s) to match or attain the desired profiles, e.g., the profiles shown in part (b) of FIG. 3. In this case, the profile corresponding to the device forming a beam along the normal to the exit aperture (0 degree steering) is implemented. Rotations of the flexible element about the x direction may be used to approximate the topology of the flexible element used for other steering angles. Part (b) of FIG. 3 illustrates this example for a steering angle of 15 degrees. The compromise is a small reduction in the steerable angle (5 degrees) due to the rotated element being raised more than its ideal surface.

Nevertheless, the example device maintains its ability to steer directive ultrasound beams over the range of −15 to +15 degrees.

The disclosed devices are capable of broadband wave front manipulation. Further details regarding such broadband capability are provided below in connection with one or more examples.

Figure 4:
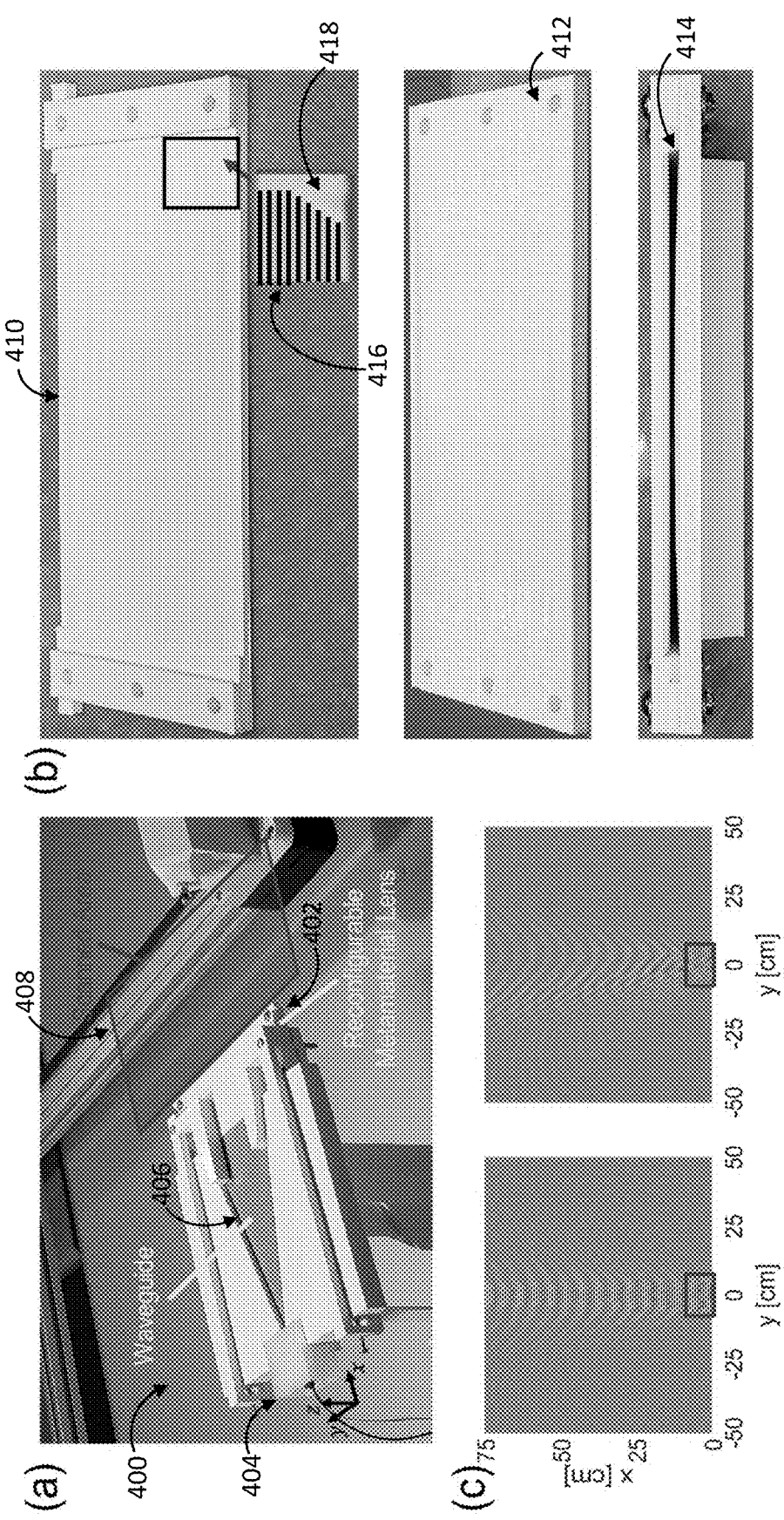
FIG. 4 depicts perspective views of an acoustic device having a metamaterial acoustic lens with a gradient index profile for beam steering in accordance with one example, along with graphical plots of acoustic pressure fields generated by the metamaterial acoustic lens.

Part (a) of FIG. 4 depicts an example device 400 for evaluating the performance of a bulk metamaterial lens 402 of the device 400. In this example, an ultrasonic transducer 404 (Murata MA40S4S) is located at the narrower end of a funnel-shaped parallel plate waveguide 406. The transducer 404 emitted an omnidirectional pulse centered at 40 kHz into the funnel-shaped parallel plate waveguide 406. The waveguide 406 guides the sound towards the input aperture of the reconfigurable metamaterial lens 402. The pulses propagated through the waveguide 406 and entered the metamaterial-based lens 402, which transformed the waves to plane waves with different directions, transmitting them into the open air. The spatial-temporal distribution of the beam formed by the lens 402 is measured in a highlighted region 408 using a broadband microphone.

Part (b) of FIG. 4 shows the metamaterial structure and assembly of the lens 402 in this example. The lens 402 includes a fixed element (top) 410 and a mobile element (middle) 412. The assembled lens 402 is also shown to depict a slit 414 through which sound enters the metamaterial-based lens 402. The fixed (top) and movable components (middle) 410, 412 are placed one on top of one another to form the ultrasonic lens 402. The slit 414 between the two components 410, 412 is also representative of the output aperture of the lens 402.

A portion of the fixed component 410 is shown in greater detail. In this example, the fixed component 410 includes an array of fin-shaped projections 416. The fin-shaped projections 416 are highlighted for ease in depicting how each fin-shaped projection 416 is disposed along a respective row as shown. The fixed component 410 also includes an impedance matching section 418 in which the height (or length) of the fins is progressively varied. In the detailed portion of FIG. 4, the rows of the fin-shaped projections 416 in the impedance matching section 418 appear to be progressively shorter, when, in fact, all of the rows shown have the same length. The appearance results from the variance in height (or length of projection) of the fins and the particular perspective view of FIG. 4 portion.

Part (c) of FIG. 4 shows measured acoustic pressure fields in front of the lens 402 for steering angles of 0 and 15 degrees (see highlighted regions). These measured fields were propagated numerically in the far-field using the Green's function method. The results show collimated, highly directive beams propagating in the desired directions.

Figure 5:
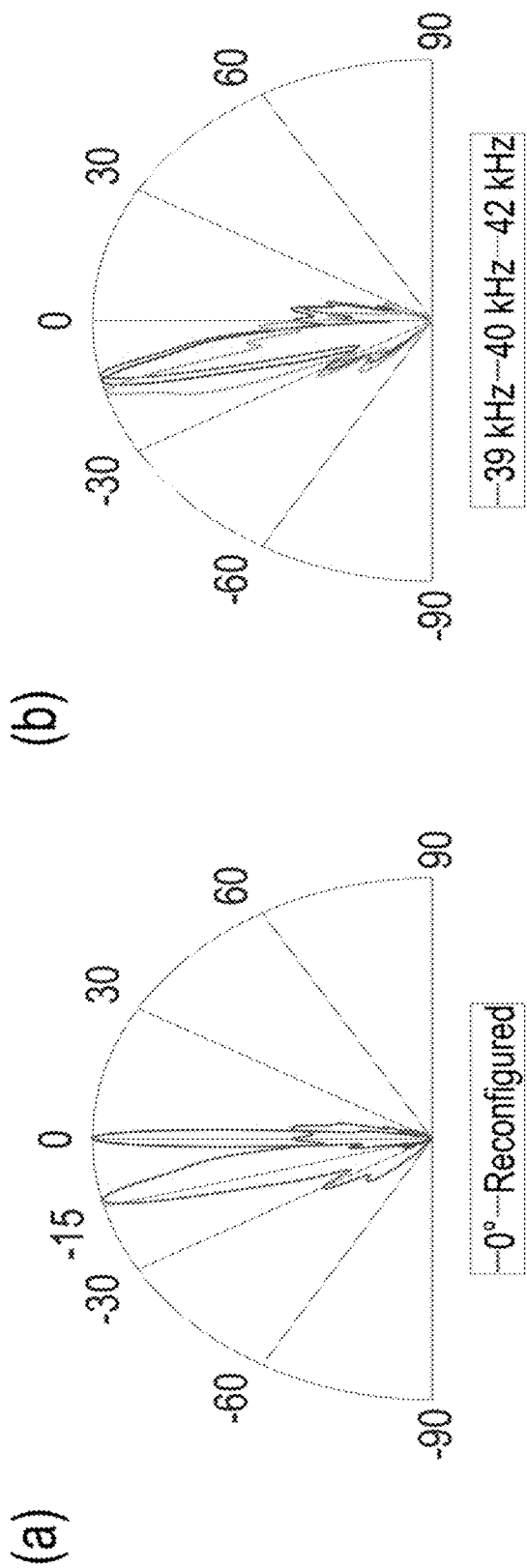
FIG. 5 depicts graphical, polar plots of far-field pressure distributions for acoustic devices having a metamaterial acoustic lens with a gradient index profile for beam steering in accordance with one example.

Part (a) of FIG. 5 shows the polar plots of the far-field pressure distributions generated by the example device 400 of FIG. 4. The distributions were measured 25 cm (29 wavelengths) away from the lens 402 (FIG. 4). The distributions were normalized to the fields measured after replacing the lens 402 with a parallel-plate waveguide of the same vertical extent. The measurements confirm the excellent directivity of the collimated beams produced by the metamaterial-based device 400 for all directions of propagation (the extreme 0 and 15 degree cases are shown in the figure) while maintaining negligible unwanted side lobes.

Additionally, the broadband performance of the metamaterial of the disclosed devices was confirmed to validate its ability to manipulate the short pulses typically used in acoustic applications such as medical imaging and sonar. Part (b) of FIG. 5 shows the representative case of a 15 degree beam angle for frequencies between 39 and 42 kHz, which confirms that the beam performance is preserved over a 7% band. Numerical simulations suggest that the lens is even more broadband, e.g., having a band of 30%.

The disclosed devices present a technique to reconfigure the acoustic behavior of bulk metamaterials using only one actuation element (controller), which allows setting desired spatial distributions of material parameters of large metamaterial structures or assemblies. The reconfiguration involves a unit cell that includes two components, e.g., one fixed and one mobile. The cell may be configured such that small actuations of the mobile component result in significant phase changes as sound propagates through the cell. When these cells are arranged to form a metamaterial, the mobile components form a single flexible element whose spatial topology can be controlled in real-time to manipulate the spatial acoustic properties of the metamaterial.

The examples described herein exhibit a low loss, large aperture beam forming and steering device operating in a 10% bandwidth centered at 40 kHz. The large aperture resulted in a narrow beam with small side lobes projected by the device and therefore the device has a very high gain. The device was configured to minimize the insertion loss by lowering the thermoviscous absorption, which is a significant challenge in the ultrasound regime, and through the use of metamaterial matching layers. In some cases, the metamaterial reconfiguration is implemented through rotation of a bottom plate having a carefully designed topology. Thus, in some cases, the bottom plate may be stiff with a non-flat surface, the rotation of which may achieve the movement depicted in, for instance, part (c) of FIG. 3. In other cases, such movement may be achieved by vibrating a flat component. Rotations of this plate of less than 1.7 degrees support redirection of the narrow beam in prescribed directions covering a range of 30 degrees. As a result, 12 such devices placed in a circular pattern (and thus having a total of 12 controllers) are enough to cover the entire range of 360 degrees.

The ability to control the material parameters in large volumes enables significant acoustic phase front manipulations without the use of resonances, and thus solves one of the most fundamental limitations of thin acoustic metamaterials (metasurfaces). The latter need resonances to implement the acoustic wave manipulation over the short distance of several unit cells, and thus have narrow operational bandwidths, e.g., often under 1%. Therefore, they are not suitable for most acoustics applications, such as sonar and medical imaging, which rely on broadband pulses. The ability to manipulate acoustic waves in real time in much thicker devices means that each unit cell is allowed to produce a much weaker response than can be realized with non-resonant structures, while maintaining overall functionality. Consequently, the disclosed devices are capable of accommodating a desired bandwidth of ultrasound applications, as well as applications typically entrusted to electromagnetic waves such as object identification, target tracking, and landscape mapping.

Figure 6:
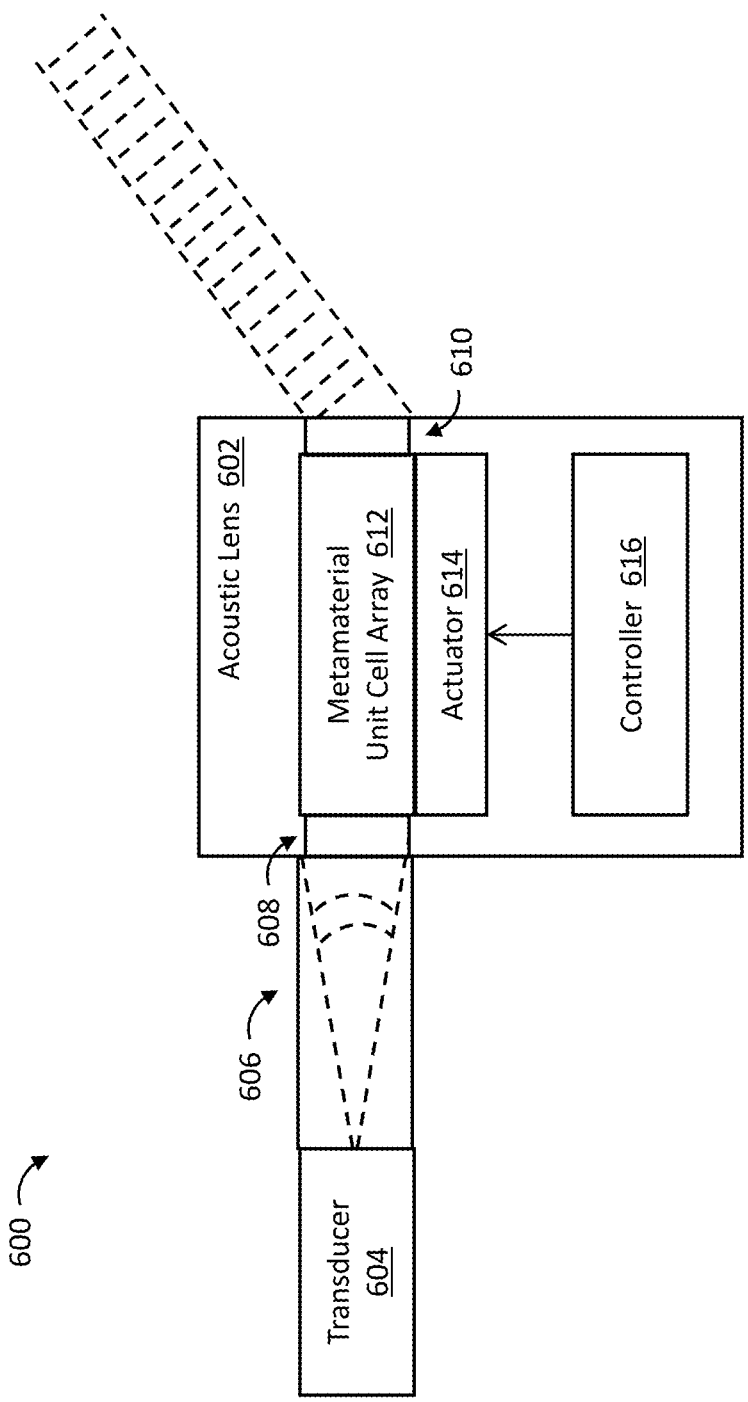
FIG. 6 depicts a block diagram of an acoustic device having a metamaterial acoustic lens in accordance with one example.

FIG. 6 depicts an acoustic device 600 in accordance with one example. The device 600 includes an acoustic lens or beam former 602. The acoustic lens 602 may be configured as described herein. The device 600 includes a transducer 604 configured to generate an input sound wave. In this example, the transducer 604 is or otherwise includes a point source such that the input sound wave is cylindrical. The device 600 also includes a waveguide 606 coupled to the transducer 604 to receive the input sound wave. In some cases, the waveguide 606 is or otherwise includes a parallel plate waveguide configured to direct the input sound wave to the acoustic lens 602.

The acoustic lens 602 includes an input aperture 608 coupled to the waveguide 606, an output aperture 610, and a gradient index lens assembly 612 disposed between the input and output apertures. As described herein, the gradient index lens assembly 612 is or otherwise includes a metamaterial-based unit cell array. In some cases, the gradient index lens assembly includes a first plate or other structure, a second plate or other structure spaced from the first structure, and an array of fins or other projections disposed between the first and second structures. As described herein, each projection of the array of projections extends from the first structure toward the second structure to define a respective gap between the projection and the second structure. As also described herein, each projection of the array of projections is configured to define a respective unit cell, with each unit cell having a sub-wavelength size relative to the acoustic beam to establish an effective refractive index profile for the acoustic beam between the first and second structures.

The acoustic lens 602 (and/or the gradient index lens assembly 612) also includes an actuator 614 configured to move the first structure, the second structure, or the array of projections for collective adjustment of the respective gaps of the array of projections. The actuator 614 is configured such that the collective adjustment of the respective gaps varies across the array of projections to spatially modify an effective refractive index of the gradient index lens. The actuator is configured such that the collective adjustment of the respective gaps varies across the array of projections to spatially modify the effective refractive index profile to steer the acoustic beam.

In the example of FIG. 6, the actuator 614 is controlled or driven by a controller 616. The controller 616 may be or otherwise include a microcontroller, a field programmable gate array (FPGA), or other processor. The actuator 614 and the controller 616 may be integrated to any desired extent.

In some cases, the actuator 614 is configured to move the second structure. For instance, the actuator 614 may act on a flexible plate or other component, such as the flexible bottom described hereinabove. In some cases, the actuator 614 may rotate the plate or other structure. The rotation may be about an axis parallel to a propagation direction of the acoustic beam prior to steering.

In other cases, the actuation may involve or include piezoelectric deformation of one or more structures. For instance, one of the first and second structures may include an array of piezoelectric patches or other elements. Pairs of the patches are disposed on opposite sides of a plate or other central structure. The actuator may include a voltage source configured to apply a position-dependent voltage across the pair of piezoelectric elements. The array may be used to vibrate one of the structures, e.g., the structure without the fins or other projections. The vibration mode may vary in the direction of sound propagation and/or the direction transverse to the direction of sound propagation.

In some cases, a voltage is applied to create a piezoelectric force that excites a mode of the lens (e.g., one of the plates). The mode shape may not be constant over space. For instance, the mode may have locations of larger displacement and locations of lower displacement. The shape of the mode may be tailored, e.g., by tailoring the mass and stiffness distribution (in space, e.g., x, y, z) in the plate. Hence the applied voltage creates a motion that is tailored as desired. Hence, in such cases, a single voltage creates a displacement correlated in space, but not constant in space (with a desired spatial distribution).

The actuator 614 may act on the structure(s) of the assembly directly or indirectly. For instance, the actuator 614 may include a plate that acts on one of the first and second structures.

As described herein, the collective adjustment of the respective gaps implemented by the actuator 614 may vary in a direction transverse to a propagation direction of the acoustic beam prior to steering.

As described and shown in connection with FIG. 3, the respective length (or height) of the projections in the array may vary along a propagation direction of the acoustic beam to provide impedance matching. For instance, the array of projections may include input and output impedance matching sections at the input and output apertures 608. 610, respectively. In some cases, the respective heights of the projections in the input and output impedance matching sections progressively range up to, and down from, a primary height of the projections, respectively.

Figure 7:
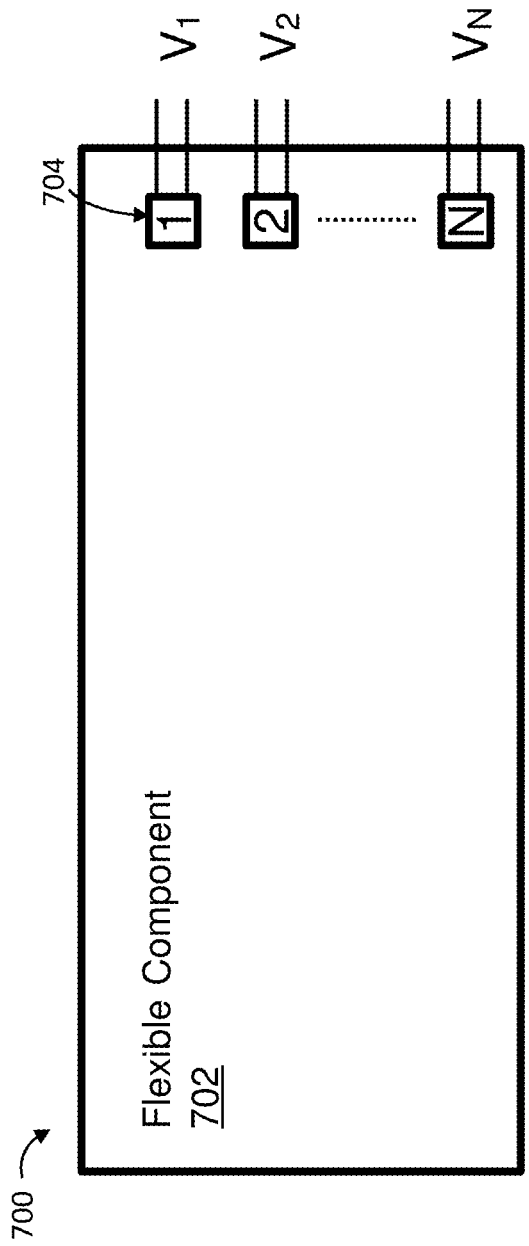
FIG. 7 depicts a schematic view of an acoustic lens having an array of piezoelectric patches driven by a plurality of voltage sources in accordance with one example.

FIG. 7 depicts an acoustic lens 700 that includes a plate or other structure 702 (e.g., a flexible component of the acoustic lens) with an array of piezoelectric patches 704 in accordance with one example. In this case, an actuator of the acoustic lens 700 includes a plurality of voltage sources ($V_1$, $V_2$, ... $V_N$) configured to apply a position-dependent voltage to the array of piezoelectric patches 704. Each patch 704 may thus be driven by a respective voltage source of the plurality of voltage sources. As described herein, the acoustic lens 700 includes an array of projections (not shown in FIG. 7) that define respective gaps. The number of projections may exceed (e.g., greatly exceed) the number of piezoelectric patches. Consequently, the array of piezoelectric patches are arranged to vibrate or otherwise move the structure for the collective adjustment of the gaps, as opposed to moving each projection individually.

The multiple voltage sources and corresponding patches of the actuator may implement the collective adjustment of the gaps by imposing a vibration mode on the plate or other flexible structure or component. Using multiple voltage sources and corresponding patches allows a wide variety of vibration modes to be realized, many of which could not be excited by a single piezoelectric actuator alone. The arrangement of patches and/or voltage sources may vary from the example shown. For instance, each voltage source may or may not be independent of the other voltage sources.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. An acoustic lens to steer an acoustic beam propagating through the acoustic lens, the acoustic lens comprising:
   a first structure;
   a second structure spaced from the first structure;
   an array of projections disposed between the first and second structures, each projection of the array of projections extending from the first structure toward the second structure to define a respective gap between the projection and the second structure; and
   an actuator configured to move the first structure, the second structure, or the array of projections for collective adjustment of the respective gaps between the projections and the second structure;

wherein each projection of the array of projections is configured to define one or more respective unit cells, each unit cell having a sub-wavelength size relative to the acoustic beam to establish an effective refractive index profile for the acoustic beam propagating through the acoustic lens between the first and second structures, and wherein the actuator is configured such that the collective adjustment of the respective gaps varies across the array of projections to spatially modify the effective refractive index profile for the acoustic beam to steer the acoustic beam.

2. The acoustic lens of claim 1, wherein the actuator is configured to move the second structure.

3. The acoustic lens of claim 1, wherein one of the first and second structures is flexible.

4. The acoustic lens of claim 1, wherein the actuator is configured to rotate one of the first and second structures about an axis parallel to a propagation direction of the acoustic beam so as to steer the acoustic beam.

5. The acoustic lens of claim 1, wherein:
one of the first and second structures comprises an array of piezoelectric patches; and
the actuator comprises a plurality of voltage sources configured to apply a position-dependent voltage to the array of piezoelectric patches.

6. The acoustic lens of claim 1, wherein the actuator comprises a plate that acts on one of the first and second structures.

7. The acoustic lens of claim 1, wherein the collective adjustment of the respective gaps varies in a direction transverse to a propagation direction of the acoustic beam prior to steering.

8. The acoustic lens of claim 1, wherein:
each projection of the array of projections has a respective length; and
the respective length of the projections varies along a propagation direction of the acoustic beam to provide impedance matching.

9. The acoustic lens of claim 1, wherein:
the first and second structures define input and output apertures through which the acoustic beam enters and exits the slot acoustic lens, respectively;
the array of projections comprises input and output impedance matching sections at the input and output apertures, respectively; and
the projections have respective heights in the input and output impedance matching sections that progressively range up to, and down from, a primary height of the projections, respectively.

10. The acoustic lens of claim 1, wherein the first and second structures comprise first and second plates, respectively.

11. The acoustic lens of claim 1, wherein the array of projections are disposed in a periodic arrangement.

12. The acoustic lens of claim 1, wherein the collective adjustment establishes that sizes of the respective gaps between the projections and the second structure vary across the array of projections.

13. The acoustic lens of claim 1, wherein:
the first structure and second structure are spaced apart from one another to define a slot; and
the array of projections are disposed in the slot.

14. The acoustic lens of claim 1, wherein the respective gaps are oriented orthogonally to a propagation direction of the acoustic beam.

15. An acoustic device comprising:
a transducer configured to generate an input sound wave;
a waveguide coupled to the transducer to receive the input sound wave; and
a beam former comprising an input aperture coupled to the waveguide, an output aperture, and a gradient index lens disposed between the input and output apertures, the gradient index lens having a continuous refractive index profile;
wherein the gradient index lens comprises:
a first structure;
a second structure spaced from the first structure;
an array of projections disposed between the first and second structures, each projection of the array of projections extending from the first structure toward the second structure to define a respective gap between the projection and the second structure; and
an actuator configured to move the first structure, the second structure, or the array of projections for collective adjustment of the respective gaps between the projections and the second structure, and
wherein the actuator is configured such that the collective adjustment of the respective gaps varies across the array of projections to spatially modify an effective refractive index of the gradient index lens.

16. The acoustic device of claim 15, wherein the transducer is a point source such that the input sound wave is cylindrical.

17. The acoustic device of claim 15, wherein the waveguide comprises a parallel plate waveguide configured to direct the input sound wave to the input aperture of the acoustic lens.

18. The acoustic device of claim 15, wherein the actuator is configured to rotate one of the first and second structures about an axis parallel to a propagation direction of the input sound wave.

19. The acoustic device of claim 15, wherein the collective adjustment of the respective gaps varies in a direction transverse to a direction of propagation through the input aperture.

20. The acoustic device of claim 15, wherein:
each projection of the array of projections has a respective length; and
the respective length of the projections varies along a propagation direction of the input sound wave to provide impedance matching.

21. The acoustic device of claim 15, wherein:
the array of projections comprises input and output impedance matching sections at the input and output apertures, respectively; and
the projections have respective heights in the input and output impedance matching sections that progressively range up to, and down from, a primary height of the projections, respectively.

22. The acoustic device of claim 15, wherein the first and second structures comprise first and second plates, respectively.

23. The acoustic device of claim 15, wherein the array of projections are disposed in a periodic arrangement.

* * * * *